United States Patent [19]
McCall

[11] 3,981,935
[45] Sept. 21, 1976

[54] AZEOTROPIC NITRATION OF BENZENE

[75] Inventor: Robert McCall, Newark, Del.

[73] Assignee: E. I. Du Pont de Nemours and Company, Wilmington, Del.

[22] Filed: Dec. 10, 1975

[21] Appl. No.: 639,875

[52] U.S. Cl. .............................................. 260/645
[51] Int. Cl.² ....................................... C07C 79/10
[58] Field of Search .................................. 260/645

[56] References Cited
OTHER PUBLICATIONS

Urbanski, Chemistry and Technology of Explosives, vol. 1, The MacMillan Co., New York, 1964, pp. 232 to 233.

Primary Examiner—Leland A. Sebastian

[57] ABSTRACT

A duplex process for the mononitration of benzene wherein the nitration is carried out in an azeotropic first stage followed by a lower temperature, mixed-acid second stage. The azeotropic stage uses reaction temperatures of at least 120°C in mixed $HNO_3$—$H_2SO_4$, and excess water is carried overhead as an azeotrope with part of the benzene and is then decanted from the benzene. The nitrated benzene is removed as bottoms and decanted from the acid phase, avoiding the necessity of reconcentrating the $H_2SO_4$. Both the nitrated benzene bottoms and the organic, benzene-containing part of the overhead stream are supplied to the second stage for completing the conversion into mononitrobenzene in mixed acid at lower temperatures such as 70°C.

15 Claims, 1 Drawing Figure

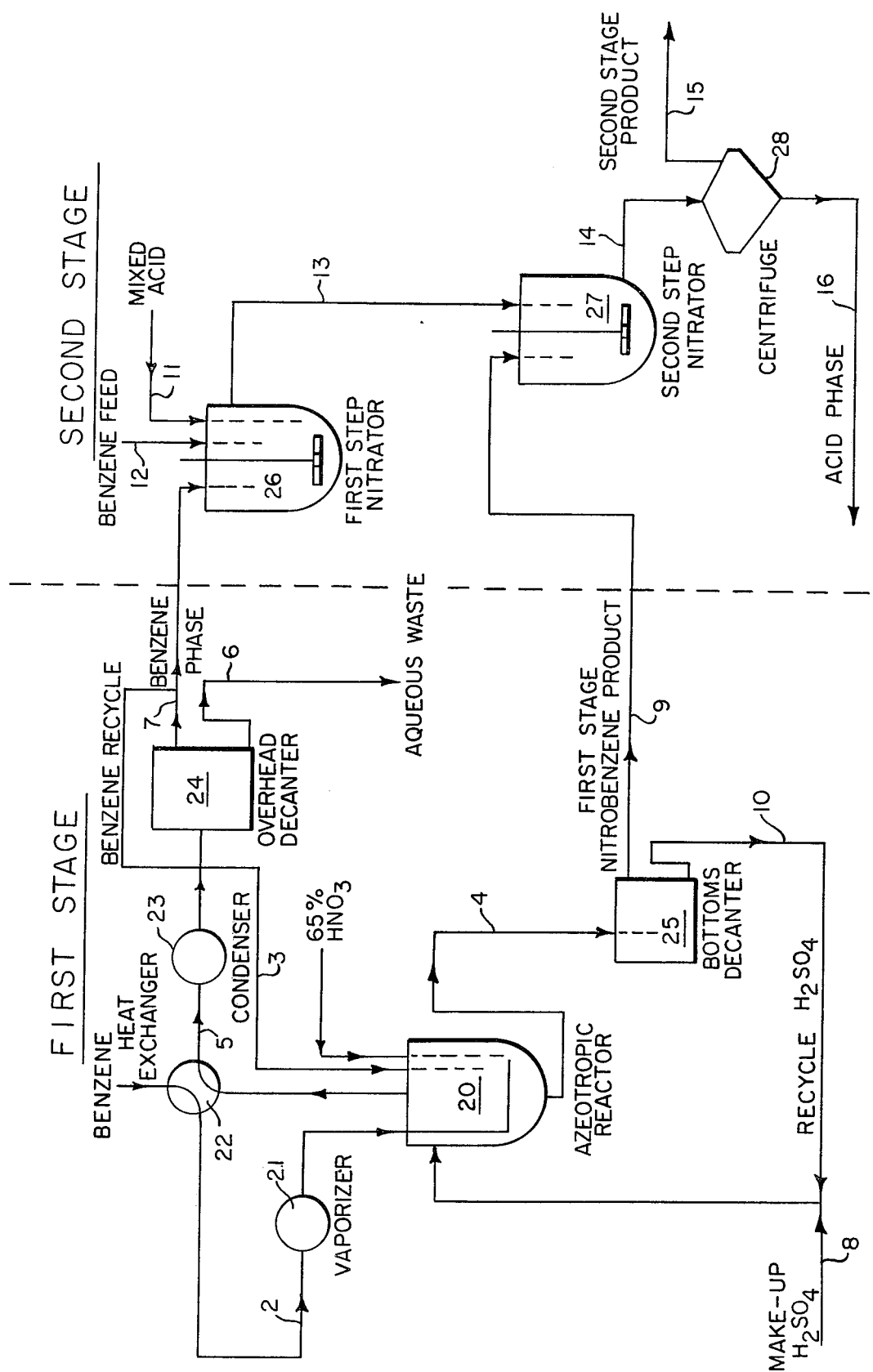

AZEOTROPIC NITRATION OF BENZENE

CROSS REFERENCE TO RELATED APPLICATION

The present invention is an improvement over U.S. application Ser. No. 497,047, filed Aug. 9, 1974 now U.S. Pat No. 3,928,475 in the name of Mark W. Dassel and assigned to the assignee of the present invention. That application is incorporated herein by reference.

BACKGROUND OF THE INVENTION

1. Field of the Invention

This invention relates to a process for the nitration of benzene. More particularly, it relates to a two-stage process for the mononitration of benzene in mixed acids.

2. Description of the Prior Art

The nitration of aromatic hydrocarbons is a process of great commercial importance. Of particular importance is the mononitration of benzene.

A number of processes have been developed for nitrating aromatic hydrocarbons. Historically, the preparation of mononitrobenzene, sometimes referred to herein as nitrobenzene, has been a batch process, a typical nitrating agent being a mixed acid initially of about 32 percent $HNO_3$, 60 percent $H_2SO_4$ and 8 percent water. (All parts, percentages and proportions herein are by weight except where indicated otherwise.) The reaction is highly exothermic, and the process is potentially explosive. For a variety of reasons— one of which is safety—the reaction has been controlled by slowly feeding one of the reactants to the other, and removing the reaction heat by external cooling. The initial reaction temperature is about 60°C. but is allowed to rise to about 90°C. near the end of the reaction period. As is well known, the final reaction mass is a two-phase system of nitrobenzene and sulfuric acid diluted with by-product water. The sulfuric acid can be separated by decantation and, for economic reasons, must be denitrated and reconcentrated, a process which involves substantial costs.

Another process for the production of nitrobenzene is disclosed in U.s. Pat. No. 2,256,999 to Castner (1941). In the Castner process, the mixed acid initially contains less than 10 percent $HNO_3$, preferably 2 to 6 percent $HNO_3$. The initial reaction temperature is about 90°C. (obtained by mixing the $H_2SO_4$ and $HNO_3$), and final reaction temperature is about 110°C. The small amount of $HNO_3$ facilitates its complete reaction with the organics. This avoids the need for denitrating the acid before it is reconcentrated, and it permits conservation of the heat of reaction in the recycled acid.

In addition to batch processes with mixed acids, nitrobenzene has also been made in continuous mixed acid processes and in nitric acid processes not using sulfuric acid. One such continuous process uses two back-mixed reactors in series operating at a temperature maintained near 70°C. by cooling, followed by centrifugal separation of the product from the acids, water washing, neutralization and finally distillation.

U.S. Pat. No. 2,773,911 — Dubois et al. (1956) describes a continuous process operating at 46° to 93°C. for the mixed acid nitration of benzene. The reactor effluent is separated into two phases comparable to the phases occuring in batch nitrations. These phases are processed to purify the nitrobenzene and reconcentrate the spent acid.

Nitric acid alone without sulfuric acid was used in the nitration of benzene with the excess water being removed overhead as an azeotrope with benzene as reported by Othmer et al., Industrial Engineering Chemistry 34, 286 (1942). Subsequently, others also worked with azeotropic removal of water from a nitration in nitric acid alone. U.S. Pat. Nos. 2,435,314 and 2,435,544 — Kokatnur (1948) say that the distillation avoids the need for the dehydrating effect of sulfuric acid. Although those patents show some nitrations at temperatures of 130° to 150°C., benzene nitration is done at temperatures up to 100°C.

U.S. Pat. No. 2,739,174 — Ross (1956) nitrates benzene or toluene at 100° to 120°C. with nitric acid only and uses azeotropic distillation of a bottoms stream to separate the nitrated hydrocarbon and water from the $HNO_3$.

However, all of these processes using nitric acid alone without sulfuric acid are less than optimum in commercially important features such as reaction rate. The temperature of the reaction is limited to minimize hazards and the production of oxidation products such as dinitrophenol by the low concentration nitric acid.

An attempt to combine mixed acid nitration and azeotropic distillation of water and benzene is shown in U.S. Pat. No. 2,370,558 — Mares (1945). The mononitration of benzene in batch and continuous processes is shown at temperatures in the range of 45° to 60°C., and it is stated that it could be done at from 40° to 90°C. Vacuum is used to aid in distilling off the azeotrope of water and benzene. Higher temperature reactions are said to be hazardous and difficult to control. Alternatively, after separation of the unwanted water, distillation can be stopped and the pressure increased to atmospheric to complete nitration at 55° to 60°C. in an hour in a batch process. However, reaction rates using these processes are not as rapid as would be desired for modern-day operations.

Accordingly, it would be desirable to find a process which can operate more efficiently and at a higher production rate than the prior art while not being hazardous.

SUMMARY OF THE INVENTION

The present invention provides an improved continuous process for the mononitration of benzene. The basic process, referred to herein as the first stage, comprises the steps of:

feeding fresh benzene and nitric acid in about stoichiometric proportions to produce nitrobenzene into a first-stage reaction vessel containing nitrobenzene, benzene and sulfuric acid;

mixing the ingredients in the reaction vessel and reacting benzene and nitric acid at a temperature in the range of about 120° to 160°C.;

vaporizing an azeotrope of a water phase containing nitric acid and a hydrocarbon phase containing benzene and nitrobenzene, and removing the azeotrope from the reaction vessel;

condensing the azeotrope and separating the aqueous phase from the hydrocarbon phase;

feeding excess benzene into the reaction vessel to maintain the total input of benzene to the reaction vessel above stoichiometric relative to the nitric acid fed thereto and to enhance the vaporization of the azeotrope, said excess benzene being either recycle stream of the hydrocarbon phase from the condensed azeotrope, or fresh benzene, or a combination of both; and withdrawing from the reaction vessel a mixture of acids and a first-stage nitrobenzene product phase, separating the nitrobenzene product phase and recycling the acids to the reaction vessel;

with the sulfuric acid concentration in the reaction vessel being controlled within the range of 55 to 70 percent by weight relative to the sulfuric acid plus water present by adjusting one or more of the reaction temperature and the rates of feeding nitric acid and benzene to the reaction vessel.

The improvement comprises feeding to at least one second-stage reaction vessel at least about half of the hydrocarbon phase separated from the aqueous phase of the azeotrope, said second-stage reaction vessel containing nitrobenzene, benzene, nitric acid and sulfuric acid, wherein the benzene contained in said hydrocarbon phase is reacted with nitric acid at a temperature in the range of about 65° to 75°C. to produce a second-stage nitrobenzene product. In a preferred embodiment of the invention, the nitrobenzene product phase of the first stage is also fed to the second stage for further reaction rather than being separately refined or used. Preferably the product of the second stage is centrifuged or settled to separate the nitrobenzene product phase from the acid phase and then the product is water washed, neutralized and distilled to purify the nitrobenzene.

In the first stage the azeotrope is taken off overhead, condensed and then separated into aqueous and hydrocarbon phases, preferably by decantation. The acids and nitrobenzene are also preferably separated from the bottoms stream by decantation. Heating and mixing of the ingredients in the reaction vessel can be aided by sparging benzene which is partially or entirely gaseous up through the other ingredients in liquid form.

The concentration of the sulfuric acid in the reaction vessel can be kept relatively constant by decanting off from the azeotrope condensed overhead an amount of water about equal to the amount of water added to the reaction vessel with the nitric acid and that produced by the chemical reaction of nitric acid and benzene.

Various feedbacks can be used to optimize the energy and materials efficiencies of the process. Also, the azeotrope removed overhead from the reaction vessel can be distilled to lower the concentration of nitric acid before separating the hydrocarbon phase from the aqueous phase.

Preferably the pressure in the reaction vessel is kept above about 1 atmosphere and below about 2 atmospheres. Also, higher material efficiency is obtained and excessive concentrations of nitric acid in the reaction vessel can be prevented by maintaining the concentration of nitric acid in the aqueous phase of the condensed azeotrope below about 4 percent, preferably below about 2.5 percent.

By taking the overhead hydrocarbon phase to the second stage for further nitration, there is no need to vaporize part or all of it as would be required for temperature control if it were to be recirculated back to the azeotropic first-stage nitrator. However, some of it, such as up to about half, can be returned to the first-stage nitrator in liquid form if desired. It is a significant saving to be able to avoid the need to vaporize the overhead stream. Since it contains some nitric acid, the selection of corrosion resistant materials for such a vaporizer would involve significant expenses.

In the second stage, it has been found desirable to feed the azeotropic overhead hydrocarbon phase to a first nitrator which produces about 95 percent nitrobenzene and to feed the bottoms nitrobenzene product phase from the first stage to a second nitrator which converts that 95 percent nitrobenzene of the first nitrator to essentially 100 percent nitrobenzene.

BRIEF DESCRIPTION OF THE DRAWING

The sole FIGURE of the drawing is a schematic flow diagram of a process illustrating a preferred embodiment of the invention.

DETAILED DESCRIPTION

The present invention involves the discovery that continuous mixed acid mononitration of benzene can be carried out with greater efficiency than previously in a duplex or two-stage process using an azeotropic first stage with a lower temperature mixed acid second stage.

The operation of the azeotropic first stage is discussed at length in the above-identified application of Dassel and need not be repeated here.

The present invention involves taking an overhead organic stream and a bottoms nitrobenzene stream from the azeotropic first stage and further reacting them to produce more nitrobenzene in lower temperature second-stage reactors to which mixed $HNO_3$—$H_2SO_4$ is furnished. Although the azeotropic reactor also uses mixed acids, the $H_2SO_4$ is recirculated and the acid feed to the first stage is principally $HNO_3$. Fresh benzene is also fed to both stages.

The mixed-acid feed to the second stage preferably has a composition about in the range of 20 to 35 percent $HNO_3$, 70 to 50 percent $H_2SO_4$, balance water, most preferably about 32 percent $HNO_3$, 60 percent $H_2SO_4$, 8 percent water. As is known in the art, the dehydrating value of the sulfuric acid or DVS is closely related to the suitability of the mixed acid for this reaction. The DVS is calculated as the weight ratio of $H_2SO_4$ on a 100 percent basis to the amount of water brought in with the $HNO_3$ and generated in the nitration reaction of $HNO_3$ plus benzene. The DVS measures the ability of the acid to overcome the equilibrium effects of the water present to drive the nitration further toward completion. For the mononitration of benzene in the second stage of the process of this invention, the DVS should be in the range of 2.4 to 2.8.

A typical composition of the overhead organic stream of hydrocarbons separated from the aqueous phase of the azeotrope in the first stage is 18 percent nitrobenzene, 66 percent benzene, 0.4 percent $HNO_3$, balance water. Although some part of this stream less than half and typically 10 to 20 percent can be recirculated to the azeotropic reactor in liquid form to aid in temperature control, it is a significant advantage of the invention to be able to avoid the need to vaporize any part of such a recycle stream. Vaporizing at least part of the overhead stream would be important for temperature control if too much of that overhead stream were recycled to the azeotropic reactor. The corrosion problems and potential thermodynamic installibilities of such streams make it difficult and expensive to design, provide and operate vaporizers for them.

A typical composition of the bottoms nitrobenzene product stream from the first stage is 90 to 97 percent nitrobenzene, balance essentially all benzene.

The second-stage reactors of the present invention readily handle these streams.

Preferably the second stage consists of two back-mixed reactors in series, with the ingredients fed into the vicinity of an impeller which very quickly mixes them. A fresh benzene feed and a nitric acid feed to the first-step reactor are used in addition to the overhead organic stream from the azeotropic reactor.

The residence time of the ingredients in the first-step reactor of the second stage is long enough to achieve a large proportion of reaction of nitrobenzene, preferably so that about 90 to 97 percent of the product of this reactor is nitrobenzene. A residence time of 10 to 15 minutes at 70°C. with efficient mixing is suitable. Thus, the nitrobenzene content of the two feeds to the second-step reactor is in this same range, the two feeds being the product of the second-stage first-step reactor and the azeotropic first-stage nitrobenzene product.

The second step aids in completing the reaction to nitrobenzene and minimizes the chance of short circuiting of unreacted ingredients through the reactors which could happen to a small degree in a single such reactor if mixing were not perfect.

The product of the second-step reactor is then treated by known techniques, preferably by centrifuging to separate the organics from the acid phase, then treating the organic phase by two stages of countercurrent water washing followed by two stages of washing in aqueous ammonia at a concentration of up to 5 percent, preferably 3 percent. The acid phase is treated with some of the fresh benzene going to the first-step reactor to remove the remaining 3 percent or so of $HNO_3$ so that the $H_2SO_4$ can be more readily reconcentrated.

The final refined product of the second-stage reactor in the second stage is typically 99.9+percent nitrobenzene, 0.05 percent unreacted benzene and less than 0.02 percent of each of the unwanted compounds dinitrobenzene and dinitrophenol.

Turning now to the drawing, the first-stage azeotropic nitration is shown on the left; the second stage lower temperature mixed acid nitration is shown on the right; and the two are suitably interconnected to make an efficient continuous integrated process. A typical preferred process is described below. Table I presents flow rates in relative weight units for the various lines shown in the drawing with the process operating as described below.

Benzene 2 and 65 percent nitric acid 1 are fed to the azeotropic nitration reactor 20 where, at 140°C. and atmospheric pressure, they are reacted to nitrobenzene in the presence of sulfuric acid. The latent heat of the benzene, vaporized in vaporizer 21, and the exothermic heat of reaction generates a vapor stream 5 which carries away the water of reaction and the water introduced with the nitric acid. Vapor stream 5 heats the fresh benzene in heat exchanger 22 to improve the thermal efficiency of the process. This stream 5 is condensed in condenser 23, and the two phases are separated in gravity overhead decanter 24. The water phase 6 is discarded, and the organic phase 7 becomes the feed to the first-step nitration reactor 26 in the second stage. Reactor 26 is provided with an effective mixer and with heat exchanger means such as internal coils to aid in controlling the reaction temperature. A portion of stream 7 is recycled as stream 3 to azeotropic reactor 20 as a liquid for temperature control purposes.

The liquid phase 4 exiting the azeotropic reactor is separated in gravity bottoms decanter 25. The acid phase 10 is recycled to the azeotropic reactor 20, and the organic phase 9 is fed to the second-step nitration reactor 27 of the second stage, similar to reactor 26. Mixed acid 11 is fed to first-step reactor 26 to react with the benzene feed 12 and benzene phase 7 from the first stage to form nitrobenzene. The total stream 14 leaving reactor 27 is separated in rotary centrifuge 28. The organic phase 15 containing the product nitrobenzene is further purified by washing and neutralizing, as discussed above. The acid phase 16 is treated with the feed benzene 12 to the first-step nitration reactor to remove traces of nitric acid, although this is not shown in the drawing. The water of reaction is absorbed in the sulfuric acid and is later removed in sulfuric acid concentrators, not shown.

TABLE I

| STREAM NO. | 1 | 2 | 3 | FIRST STAGE 4 | 5 | 6 | 7 | 8 | 9 |
|---|---|---|---|---|---|---|---|---|---|
| Stream | Nitric Feed | Benzene Feed | Liquid Benzene | AZN Product | AZN Vapor | Decanted Organic | Make-up Acid | Organic Phase | Recycle Acid |
| Temp.,°C. | 25 | 80 | 40 | 140 | 140 | 40 | 25 | 140 | 140 |
| Lbs/Hr Avg Flow | | | | | | | | | |
| Benzene | | 1,124 | 156 | 16.2 | 943 | 942 | | 16.2 | |
| Nitrobenzene | | | 43.4 | 280 | 263 | 263 | | 280 | |
| Dinitrobenzene | | | | | | | | | |
| Dinitrophenol | | | | 1.4 | | | | 1.4 | |
| Water | 142 | | 0.4 | 140 | 214 | 2.0 | 0.6 | 0.3 | 140 |
| Nitric Acid | 265 | | | 1.1 | 5.3 | 3.2 | | 0.4 | 0.7 |
| Sulfuric Acid | | | | 262 | | | 1.9 | 1.9 | 260 |
| Total | 407 | 1,124 | 199.8 | 700.7 | 1,425.3 | 1,210.2 | 2.5 | 300.2 | 400.7 |

| Stream No. | 10 | 11 | SECOND STAGE 12 | 13 | 14 | 15 |
|---|---|---|---|---|---|---|
| Stream | Mixed Acids | Benzene Feed | First-Step Product | Second-Step Product | NB Product | Acid Phase |
| Temp., °C. | 25 | 40 | 70 | 70 | 70 | 70 |
| Lbs/Hr Avg Flow | | | | | | |
| Benzene | | 558 | 108 | 2.5 | 2.5 | |
| Nitrobenzene | | 112 | 2,648 | 3,120 | 3,092 | 27.8 |
| Dinitrobenzene | | | 2.0 | 2.8 | 2.7 | 0.1 |
| Dinitrophenol | | | | 3.3 | 3.3 | |
| Water | 797 | 0.8 | 1,141 | 1,169 | 1.3 | 1,168 |
| Nitric Acid | 1,399 | | 204 | 105 | 66.2 | 39.4 |
| Sulfuric Acid | 3,071 | 0.2 | 3,071 | 3,074 | 3.2 | 3,071 |
| Total | 5,257 | 671.0 | 7,174.0 | 7,476.6 | 3,171.2 | 4,306.3 |

What is claimed is:

1. In a two-stage continuous process for the mononitration of benzene having a first stage comprising the steps of feeding fresh benzene and nitric acid in about stoichiometric proportions to produce nitrobenzene into a first-stage reaction vessel containing nitrobenzene, benzene and sulfuric acid;

mixing the ingredients in the reaction vessel and reacting benzene and nitric acid at a temperature in the range of about 120° to 160°C.;

vaporizing an azeotrope of a water phase containing nitric acid and a hydrocarbon phase containing benzene and nitrobenzene, and removing the azeotrope from the reaction vessel;

condensing the azeotrope and separating the aqueous phase from the hydrocarbon phase;

feeding excess benzene into the reaction vessel to maintain the total input of benzene to the reaction vessel above stoichiometric relative to the nitric acid fed thereto and to enhance the vaporization of the azeotrope, said excess benzene being either recycle stream of the hydrocarbon phase from the condensed azeotrope, or fresh benzene, or a combination of both; and withdrawing from the reaction vessel a mixture of acids and a first-stage nitrobenzene product phase, separating the nitrobenzene product phase and recycling the acids to the reaction vessel;

with the sulfuric acid concentration in the reaction vessel being controlled within the range of 55 to 70 percent by weight relative to the sulfuric acid plus water present by adjusting one or more of the reaction temperatures and the rates of feeding nitric acid and benzene to the reaction vessel;

the improvement of feeding to at least one second-stage reaction vessel at least about half of the hydrocarbon phase separated from the aqueous phase of the azeotrope, said second-stage reaction vessel containing nitrobenzene, benzene, nitric acid and sulfuric acid, wherein the benzene from said hydrocarbon phase is reacted with nitric acid at a temperature in the range of about 65° to 75°C. to produce a second-stage nitrobenzene product.

2. A process according to claim 1 in which the first-stage nitrobenzene product phase is also fed to a second-stage reaction vessel.

3. A process according to claim 2 wherein the product of the second stage is centrifuged to separate the nitrobenzene product phase from the acid phase, and the product is water washed, neutralized and distilled to purify the nitrobenzene.

4. A process according to claim 2 wherein up to about half of the hydrocarbon phase separated from the aqueous phase of the azeotrope is returned in liquid form to the first-stage reaction vessel.

5. A process according to claim 4 in which the remainder of said hydrocarbon phase is fed to a first reaction vessel in the second stage containing benzene, nitrobenzene, nitric acid and sulfuric acid at a temperature in the range of about 65° to 75°C. wherein the benzene is converted to nitrobenzene to such an extent that the product of such first-step reactor is at least about 90 percent nitrobenzene, and in which said nitrobenzene product phase of the first stage and the product of the first-step reaction vessel of the second stage are both fed to a second-step reaction vessel in the second stage containing nitrobenzene, nitric acid and sulfuric acid at a temperature in the range of about 65° to 75°C. wherein the remaining benzene is converted to nitrobenzene.

6. A process according to claim 1 wherein the amount of water separated from the condensed azeotrope is about equal to the amount of water provided by the nitric acid feed and the reaction of nitric acid and benzene in the reaction vessel.

7. A process according to claim 1 in which the reaction in the first stage is conducted in the temperature range of about 130° to 150°C.

8. A process according to claim 7 in which the reaction in the first stage is conducted at about 140°C. and the concentration of the sulfuric acid in the reaction vessel is controlled at about 65 percent by weight relative to the sulfuric acid plus water present.

9. A process according to claim 1 in which the aqueous and hydrocarbon phases in the azeotrope are separated by decantation.

10. A process according to claim 1 in which the acid and nitrobenzene phases of the first stage are separated by decantation.

11. A process according to claim 1 in which at least part of the mixing of the ingredients in the reaction vessel of the first stage is achieved by sparging benzene vapor up through the other ingredients.

12. A process according to claim 1 in which the reaction of the first stage is operated at a total pressure of at least about 1 atmosphere.

13. A process according to claim 1 in which the reaction of the first stage is operated at a total pressure about in the range of 1 to 2 atmospheres.

14. A process according to claim 1 in which the nitric acid concentration in the aqueous phase of the condensed azeotrope is kept below about 4 percent by weight.

15. A process according to claim 2 in which the nitric acid concentration in the aqueous phase of the condensed azeotrope is kept below about 2.5 percent by weight.

* * * * *